(12) United States Patent
Manigoff (10) Patent No.: US 10,383,598 B2
(45) Date of Patent: Aug. 20, 2019

(54) ULTRASOUND IMAGING PROBE (71) Applicant: B-K MEDICAL APS, Herlev (DK)

(72) Inventor: Jesper L. Manigoff, Frederiksberg (DK)

(73) Assignee: B-K Medical Aps, Herlev (DK)

( * ) Notice: Subject to any disclaimer, the term of this patent is extended or adjusted under 35 U.S.C. 154(b) by 946 days.

(21) Appl. No.: 14/760,550

(22) PCT Filed: Jan. 14, 2013

(86) PCT No.: PCT/IB2013/000043
§ 371 (c)(1),
(2) Date: Jul. 13, 2015

(87) PCT Pub. No.: WO2014/108713
PCT Pub. Date: Jul. 17, 2014

(65) Prior Publication Data
US 2015/0335312 A1 Nov. 26, 2015

(51) Int. Cl.
*A61B 8/00* (2006.01)
*A61B 1/005* (2006.01)
*A61B 8/12* (2006.01)
*A61B 8/08* (2006.01)

(52) U.S. Cl.
CPC .......... *A61B 8/4461* (2013.01); *A61B 1/0052* (2013.01); *A61B 1/0057* (2013.01); *A61B 8/12* (2013.01); *A61B 8/4455* (2013.01); *A61B 8/4466* (2013.01); *A61B 8/4483* (2013.01); *A61B 8/485* (2013.01)

(58) Field of Classification Search
None
See application file for complete search history.

(56) References Cited

U.S. PATENT DOCUMENTS

| | | |
|---|---|---|
| 2005/0119568 A1 | 6/2005 | Salcudean et al. |
| 2009/0143679 A1 | 6/2009 | Salcudean et al. |
| 2010/0160778 A1 | 6/2010 | Esdandari Hani |
| 2010/0168569 A1* | 7/2010 | Sliwa .................. A61B 8/0841 600/439 |
| 2011/0166455 A1* | 7/2011 | Cully ...................... A61B 8/12 600/463 |

OTHER PUBLICATIONS

Reza Zahiri Azar, et al, Real-Time transient elastography on standard ultrasound using mechanically induced vibration: System design and initial results, Ultrasonics Syposium, 2011 IEEE International, Oct. 18, 2011, pp. 2388-2391.
PCT/IB2013/000043 International Search Report published as WO2014/108713 dated Jul. 17, 2014.

* cited by examiner

*Primary Examiner* — Patricia J Park
(74) *Attorney, Agent, or Firm* — Anthony M. Del Zoppo, III; Daugherty & Del Zoppo, Co., LPA (57) ABSTRACT

An elongate ultrasound probe (204) including a probe head (214) with a transducer array (216), a handle (208), a flexor (222) located between and affixed to the probe head and the handle, a flexor actuator (224) configured to flex the flexor, and a probe head motion actuator (226) configured to oscillate the flexor actuator and thereby oscillate the probe head. A method includes electronically vibrating a probe head, which includes a transducer array, of an ultrasound probe in connection with ultrasound elasticity imaging.

6 Claims, 6 Drawing Sheets

ULTRASOUND IMAGING PROBE

RELATED APPLICATION

This application is a national filing of PCT application Serial No. PCT/IB2013/000043, filed Jan. 14, 2013, published as WO2014/108713 on Jul. 17, 2014. This application claims priority to PCT application Serial No. PCT/IB2013/000043, published as WO2014/108713 on Jul. 17, 2014.

TECHNICAL FIELD

The following generally relates to ultrasound and more particularly to an ultrasound probe and is described with particular application to ultrasound imaging; however, the probe can be employed with other ultrasound applications.

BACKGROUND

Ultrasound (US) imaging has provided useful information about the interior characteristics of an object or subject under examination. A US imaging system has included an ultrasound probe housing a transducer array that is configured to transmit an ultrasound signal into a scan field of view and receive echoes produced in response to the ultrasound signal interacting with structure of an object or subject therein. As the ultrasound signal traverses the object or subject, portions of the ultrasound signal are attenuated, scattered, and/or reflected off structure and/or boundaries in the interior of the object or subject, with some of the reflections traversing back towards the transducer array. The later reflections (or echoes) are received at the transducer array. In B-mode imaging, the echoes correspond to an axial slice through the object or subject and are processed to generate scanlines, which are used to produce a scanplane, or a two or a three dimensional image of the slice or volume, which are displayed via a display monitor.

Figure 1A:
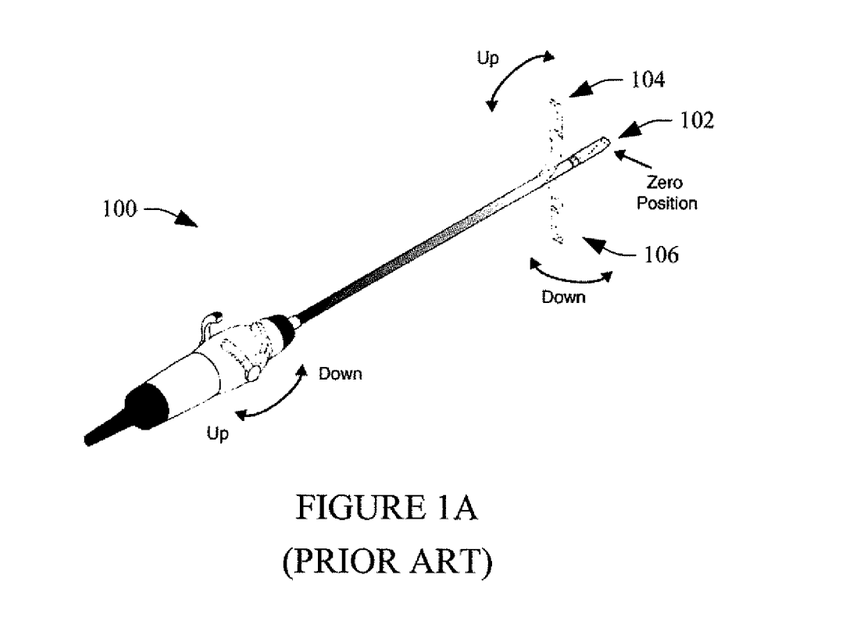
FIGS. 1A and 1B illustrate a prior art laparoscopic ultrasound imaging probe with a flexible tip.
Figure 1B:
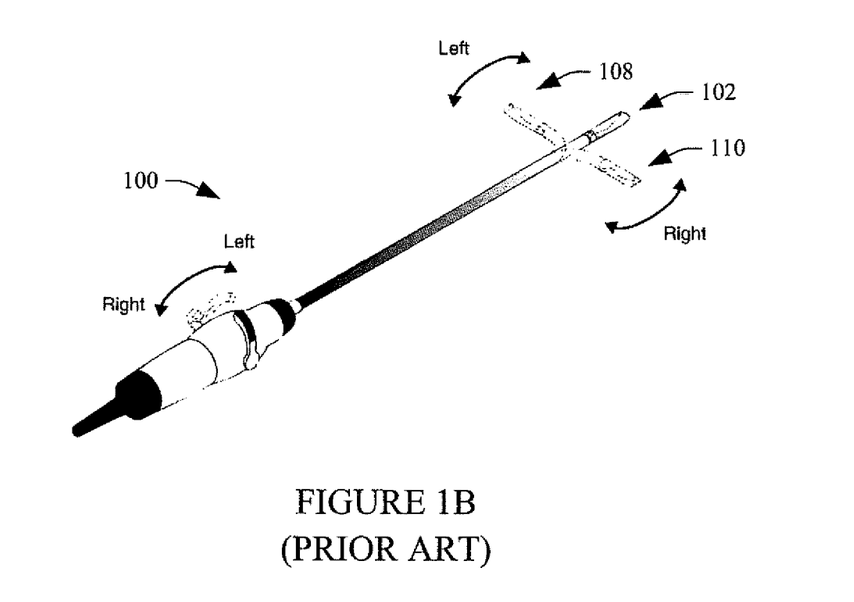

Laparoscopic ultrasound examinations have been used to detect tumors in cavities. Generally, there are two types of ultrasound imaging probes—flexible and rigid. Flexible ultrasound probes include an articulating portion that can be controllably articulated to move an end of the probe with a transducer array through an angle of up to ninety (90) degrees in one to four planes. FIGS. 1A and 1B show an example of a flexible probe 100; namely, a laparoscopic transducer type 8666, which is a product of BK-Medical ApS, a company of Herlev, Denmark, which is a wholly owned subsidiary of Analogic Corporation, a company of MA, USA. As shown in FIG. 1A, the probe 100 is configured to articulate between a zero position 102 and an up position 104 and a down position 106. As shown in FIG. 1B, the probe 100 is configured to articulate between the zero position 102 and a left position 108 and a right position 110. In contrast, rigid probes are not configured to articulate as such and remain at the zero position 102. A lab probe can also be rigid in one direction, or only have motion in one plane. Furthermore this can be combined with a rotational motion of the array (i.e., can be combined with all the above).

An indicator used to guide biopsies has been the stiffness of the tissue, as unhealthy tissue is often stiffer than surrounding healthy tissue. Tissue stiffness has been determined with ultrasound using a technique referred to as elasticity imaging. With elasticity imaging, a mechanical compression (e.g., via vibration) is applied to tissue, with the unhealthy tissue compressing less than the surrounding tissue since the strain is less than the surrounding tissue. The mechanical compression has been applied by having the user of the probe push the probe against tissue of interest in a fluctuating manner to compress (e.g., 1 mm or so) and decompress the tissue. The measured stiffness has been overplayed on top of the B-mode image. With laparoscopic imaging, there is no direct visibility of the probe and the tissue, except when used with a camera, thus making it difficult to apply suitable manual compression to the tissue. Furthermore, since flexible probes by nature can be twisted and rotated, it may be difficult to manually apply the requisite force in the right direction and in a stable recurrent manner. Moreover, the length of the transducer may make it difficult to manually apply the oscillating pressure at the tip of the probe.

SUMMARY

Aspects of the application address the above matters, and others.

In one aspect, an elongate ultrasound probe including a probe head with a transducer array, a handle, a flexor located between and affixed to the probe head and the handle, a flexor actuator configured to flex the flexor, and a probe head motion actuator configured to oscillate the flexor actuator and thereby oscillate the probe head.

In another aspect, a method includes electronically vibrating a probe head, which includes a transducer array, of an ultrasound probe in connection with ultrasound elasticity imaging.

In another aspect, an ultrasound imaging system includes an elongate ultrasound probe. The probe includes a probe head with a transducer array, a handle, a flexor located between and affixed to the probe head and the handle, and a flexor actuator configured to flex the flexor. The probe further includes a probe head motion actuator configured to oscillate the flexor actuator and thereby oscillate the probe head, and electronics, internal to the handle, that controls at least the probe head motion actuator.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

The following describes an ultrasound probe configured for at least laparoscopic elasticity imaging. Initially referring FIG. 2, an imaging system 202 such as ultrasound imaging system is schematically illustrated. The imaging system 202 includes an ultrasound probe 204 and a console 206. The probe 204 includes a handle 208, a shaft 210, an articulating member 212 and a probe head 214.

Figure 2:
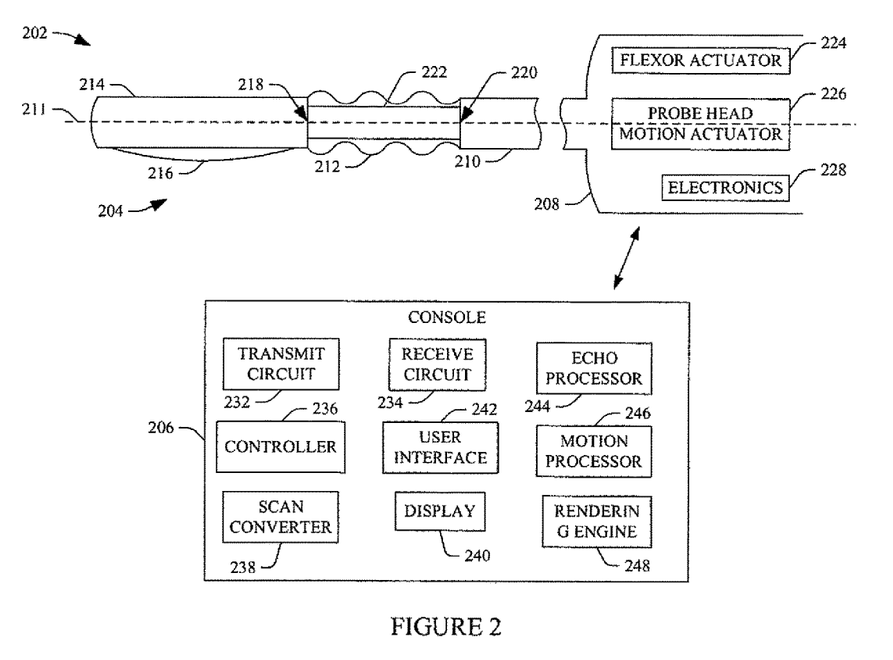
FIG. 2 schematically illustrates an example ultrasound imaging system including an ultrasound imaging probe with a probe head motion actuator that oscillates a probe head and a transducer array housed therein.

The probe head 214 includes a transducer array 216, which includes one, two or three dimensional array transducer elements. Suitable configurations include, but are not limited to, linear, curved (e.g., convex), phased and matrix arrays. The transducer array 216 can be used to acquire data for A-mode, B-mode, etc. acquisitions, individually and in combination with color flow, Doppler flow, etc.

The shaft 210 extends along a longitudinal axis 211 of the probe 204 and is geometrically configured to allow for moving and/or positioning the probe head 214 (and thus the transducer array 216 attached thereto) within a cavity, such as the abdomen or other cavity of a human patient, or a cavity of an object.

The articulating member 212 is a generally flexible section of the probe 204. A first side 218 of the articulating member 212 is affixed to the probe head 214 and an opposing side 220 of the articulating member 212 is affixed to the shaft 210.

A flexor 222 is controlled to flex the articulating member 212 to position the transducer array 216 between various positions in one to four planes through angles of up to one hundred and seventy (170) degrees and/or straight (zero degrees) along the longitudinal axis 211 of the probe 204. Examples of positions include those shown in connection with FIGS. 1A and 1B.

The handle 208 includes a flexor actuator 224, a probe head motion actuator 226, and electronics 228.

The flexor actuator 224 is configured to actuate the flexor 222 to move the head 214 and thus the transducer array 216 through the various angels discussed herein. Various approaches can be utilized to actuate the flexor 222. An example of a suitable manual approach is discussed in FIGS. 3A, 3B and 3C and used in connection with the laparoscopic transducer type 8666. In an alternative embodiment, the electronics 228 include circuitry for electronically controlling the flexor 222.

The probe head motion actuator 226 is configured to translate the flexor 222 and hence the probe head 214 and transducer array 216, e.g., when the system 202 is operated in elasticity imaging mode, e.g., in connection with a laparoscopic or other procedure. As described in greater detail below, the probe head motion actuator 226 is incorporated with and controllably oscillates (or vibrates) the flexor actuator 224 in the handle 208, which oscillates the probe head 214 and transducer array 216. Such oscillating is well-suited for applying mechanical compression or vibration to tissue for elasticity imaging.

The probe head motion actuator 226 can be controlled internally, for example, by the electronics 228 and/or by an external device. With either instance, the user and/or other personnel need only activate the motion actuator 226 to oscillate the transducer array 216, mitigating having to have the user manually push the probe head 214 against tissue of interest in a fluctuating manner to compress and decompress the tissue. This electronically controlled oscillation also facilitates applying suitable force at a suitable frequency in cavities with low to no visibility, such as with laparoscopic procedures. Examples of suitable frequencies are frequencies that will compress the tissue of interest up to two millimeters, such as 0.5 to 5.0 Hz.

The electronics 228 are in electrical communication with the ultrasound transducer array 216 and are used to convey signals to the ultrasound transducer array 216 that actuate the individual transducer elements therein to produce ultrasound signals and receive signals therefrom corresponding to received echoes. Alternatively, the electronics 228 can reside outside of the ultrasound probe 204, for example, in connection with console 206 and/or elsewhere.

It is to be appreciated that the probe 204 can be used for laparoscopic, endoscopic, and/or other ultrasound applications, and can be used to assist personnel, for example, with an interventional procedure such as a liver, gall bladder, tumor biopsy, etc., guide personnel, for example, with RF ablation, chemical injection, etc. As shown, the probe 204 is employed with the console 206. In other embodiments, the probe 204 can be employed with other consoles and/or device, via cable or wireless communication.

The console 206 includes a transmit circuit 232 that controls the phasing and/or time of actuation of the individual elements of the transducer array 216, which allows for steering and/or focusing the transmitted beam from predetermined origins along the array and at predetermined angles.

The console 206 further includes a receive circuit 234 that receives signals indicative of the echoes received by the transducer array 216. For B-mode and/or other applications, the receive circuit 234 can beamform (e.g., delays and sums) the echoes into a sequence of focused, coherent echo samples along focused scanlines of a scanplane. For elastography imaging, the echoes include tissue motion or displacement information between the frames of data.

A controller 236 controls the transmit circuit 232 and/or the receive circuit 234. Such control may include, but is not limited to, controlling the frame rate, number of scanline groups, transmit angles, transmit energies, transmit frequencies, transmit and/or receive delays, etc., and/or activating the motion actuator 226 for elasticity imaging.

An echo processor 244 processes received echoes. Such processing includes beamforming (e.g., delay and sum) the echoes in connection with B-mode imaging, etc. A motion processor 246 extracts and processes the tissue motion information from the echoes in connection with elastography imaging. Other processing lowers speckle, improves specular reflector delineation, and/or includes FIR filtering, IIR filtering, etc.

A scan converter 238 scan converts the frames of data to generate data for display, for example, by converting the data to the coordinate system of the display. This may include changing the vertical and/or horizontal scan frequency of signal based on the display. Furthermore, the scan converter 238 can be configured to employ analog and/or digital scan converting techniques.

A rendering engine 248 is configured to at least generate elastography or other images based on the processed data. The elastography images can be visually presented, stored, conveyed to another device, and/or otherwise utilized. A display 240 presents the rendered data.

A user interface 242 includes input and/or output devices for interacting with the controller 236, e.g., to select a data processing and presentation mode, a data acquisition mode (e.g., B-mode, elasticity imaging, etc.), initiate scanning, etc. The user interface 242 may include controls such as buttons, knobs, a keypad, a touch screen, etc. The user interface 242 may also include visual (e.g., LCD, LED, etc.) and/or audible displays.

In the illustrated embodiment, the probe 204 and the console 206 respectively include complementary electrical interfaces, which can be electrically connected via a cable, wireless communication, or the like. The electrical connection there between allows electrical signals to be conveyed back and forth between the probe 204 and the console 206.

It is to be understood that the relative size, shape and position of the various components of the system 202 are provided for explanatory purposes and are not limiting. In other embodiments, at least one of the size, shape and position of at least one of the components is different.

Figure 3A:
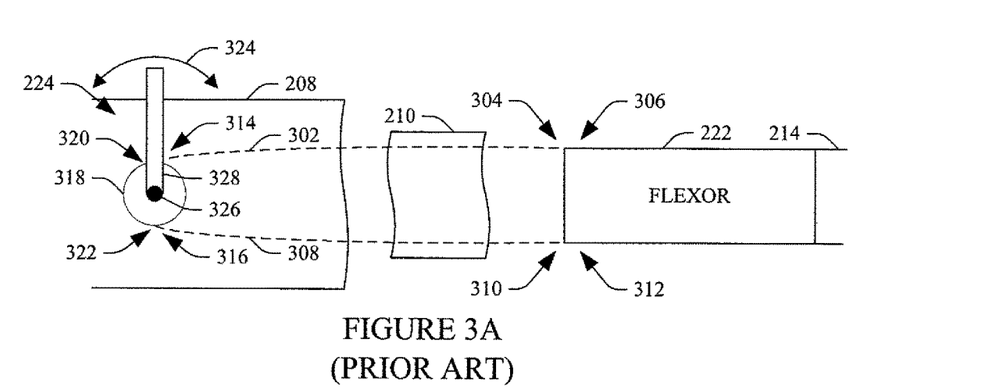
FIGS. 3A, 3B and 3C schematically illustrate a prior art flexor and flexor actuator configuration.
Figure 3B:
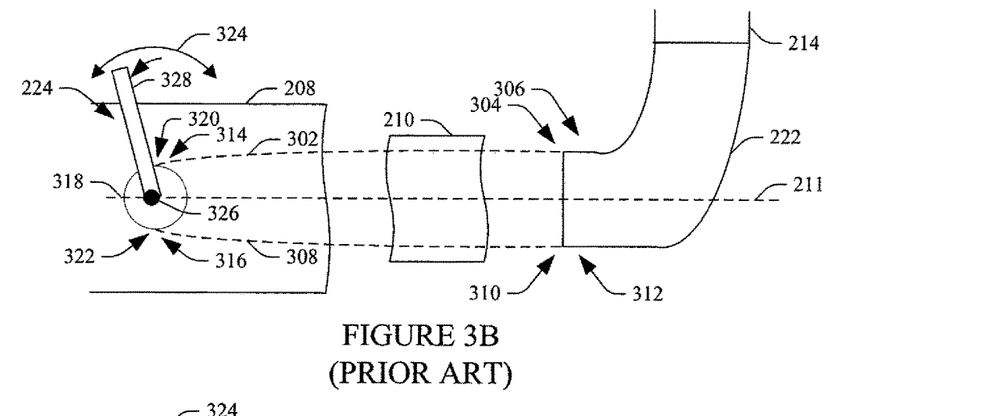
Figure 3C:
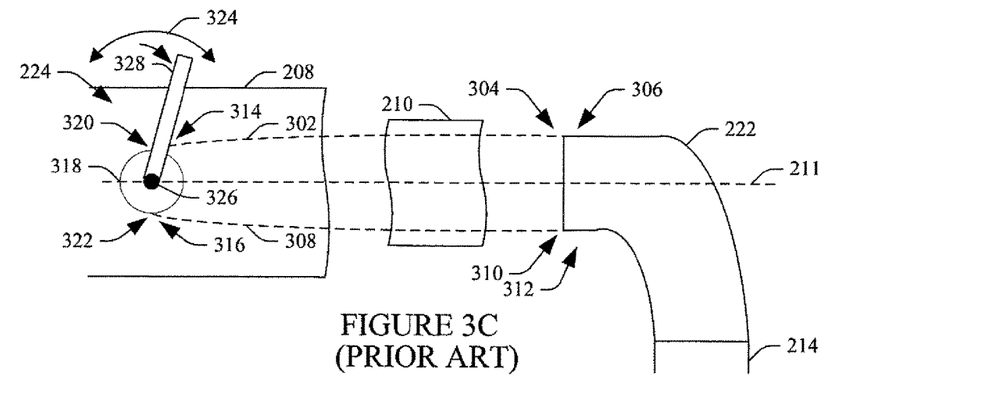

FIGS. 3A, 3B and 3C schematically illustrate an example of prior art configuration of the flexor actuator 224 in connection with the handle 208, the shaft 210, the flexor 222, and the probe head 214.

The flexor actuator 224 includes a cable 302. An end 304 of the cable 302 is affixed to a first portion 306 of the flexor 222. The flexor actuator 224 further includes a cable 308. An end 310 of the cable 308 is affixed to a second or opposing portion 312 (which opposes portion 306) of the flexor 222.

Opposing ends 314 and 316 of the cables 302 and 308 are affixed to a movable member 318, with the end 314 of the cable 302 affixed to a first region 320 of the movable member 318 and the end 316 of the cable 308 affixed to second region 322 (which opposes the region 320) of the movable member 318.

A shaft 328 is affixed to the movable member 318 and is configured to move the movable member 318. In the illustrated embodiment, the movable member 318 is circular in shape and is affixed to rotate through a predetermined angle range or arc 324 about a rotational axis 326, the shaft 328 is affixed at the rotational axis 326, and moving the shaft 328 through range of the arc 324 rotates the moveable member 318 about the rotational axis 326.

In this configuration, pivoting the shaft 328 away from the probe head 214 concurrently urges the second cable 308 in a direction towards the probe head 214 and pulls the first cable 302 in a direction away from the probe head 214. As a result, the flexor 222 is flexed such that the first portion 306 flexes away from the axis 211 and the second portion 312 flexes towards the axis 211. This is shown in FIG. 3B.

Furthermore, pivoting the shaft 328 towards the probe head 214 concurrently urges the first cable 302 in a direction towards the probe head 214 and pulls the second cable 308 in a direction away from the probe head 214. As a result, the flexor 222 is flexed such that the first portion 306 flexes towards the axis 211 and the second portion 312 flexes away from the axis 211. This is shown in FIG. 3C.

Where the cables 302 and 308 are for up/down motion, pivoting the shaft 328 as described herein flexes the probe head 214 up and down. Where the cables 302 and 308 are for left/right motion, pivoting the shaft 328 as described herein flexes the probe head 214 left and right. Although only a pair of cables 302 and 308 is shown for up/down or left/right motion, it is to be understood that there are at least two such pairs, one pair for up/down motion and another pair for left/right motion.

When the shaft 328 is pivoted to a generally central position of the arc 324, the tension on the cables 302 and 308 is approximately equal, and the probe heads 214 extends axially along the axis 211. It is to be appreciated that location and/or length of the arc 324 is not limiting. In addition, the shaft 328 could be located on the opposing side and/or otherwise shaped.

Furthermore, the moveable member 318 could instead be a slide mechanism, including two sliding members that linearly slide in opposing direction. In this manner, translating the moveable member 318 towards and away from the probe head 214 has a same effect as discussed above with respect to flexing the probe head 214.

Figure 4:
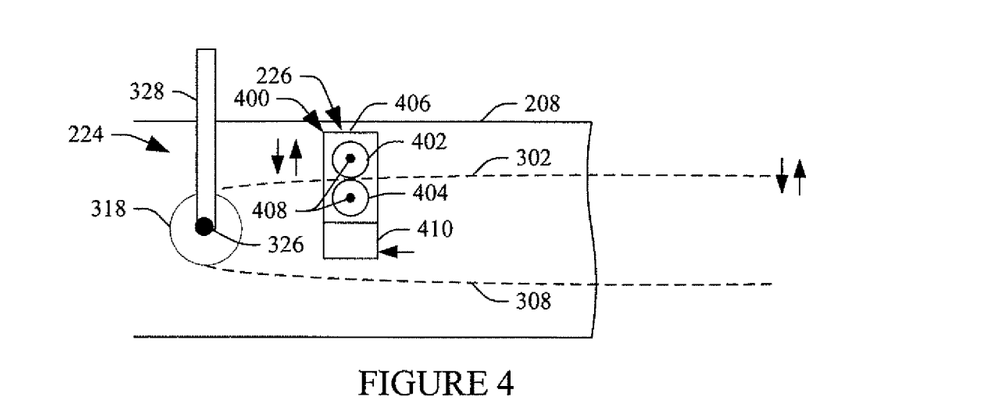
FIG. 4 schematically illustrates an example of the motion actuator.

Turning now to FIG. 4, a first example of the motion actuator 226 is illustrated.

In this example, the motion actuator 226 includes an electro-mechanical device 400 with two guides 402 and 404 located in a housing 406 and configured to roll therein. In one instance, one or more of the guides 402 and 404 rotates about a pin 408 (as shown). In another instance, the guides 402 and 404 are free floating within the housing.

As shown, the cable 302 is sandwiched between and physically contacts the guides 402 and 404. Where the guides 402 and 404 rotate, the guides 402 and 404 are set separated from each other so that the cable 302 can be fed there between. Where the guides 402 and 404 free floating, the guides 402 and 404 will move when installing the cable 302.

When pivoting the shaft 328 as discussed above, for example, towards and away from the probe head 214, the guides 402 and 404 remain at a static location, but the guides 402 and 404 roll as the cable 302 translates there between towards and away from the probe head 214.

A control portion 410, in response to an activation signal, automatically and electronically causes the guides 402 and 404 to oscillate, which causes the cable 302 to oscillate (translate back and forth, vibrate, etc.). The control portion 410 controllably oscillates the guides 402 and 404, for example, at a frequency suitable for elasticity imaging. The control portion 410 may include a device such as a piezoelectric vibration generator or the like.

The electro-mechanical device 400 can be activated via a button, knob, slider, etc. located on the probe 204. Additionally or alternatively, the electro-mechanical device 400 can be activated via the console 206. Additionally or alternatively, the electro-mechanical device 400 can be activated via a remote control. Additionally or alternatively, the electro-mechanical device 400 can be activated via other device.

Figure 5A:
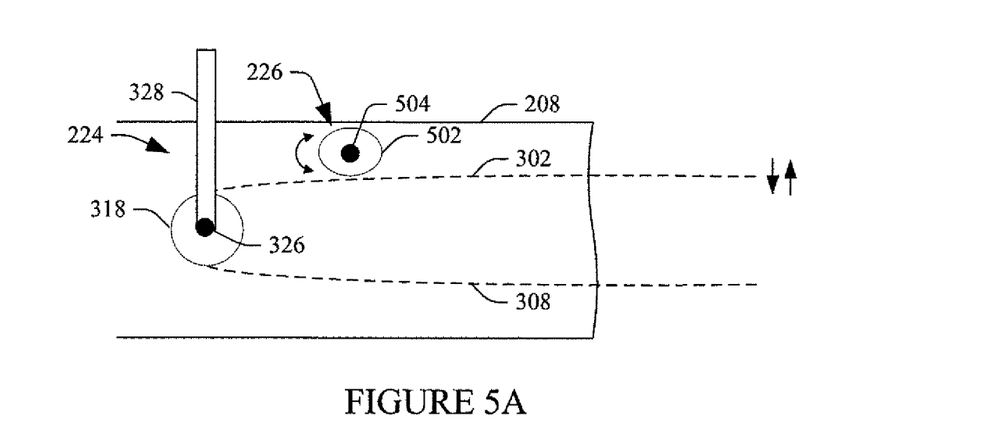
FIGS. 5A and 5B schematically illustrate another example of the motion actuator.
Figure 5B:
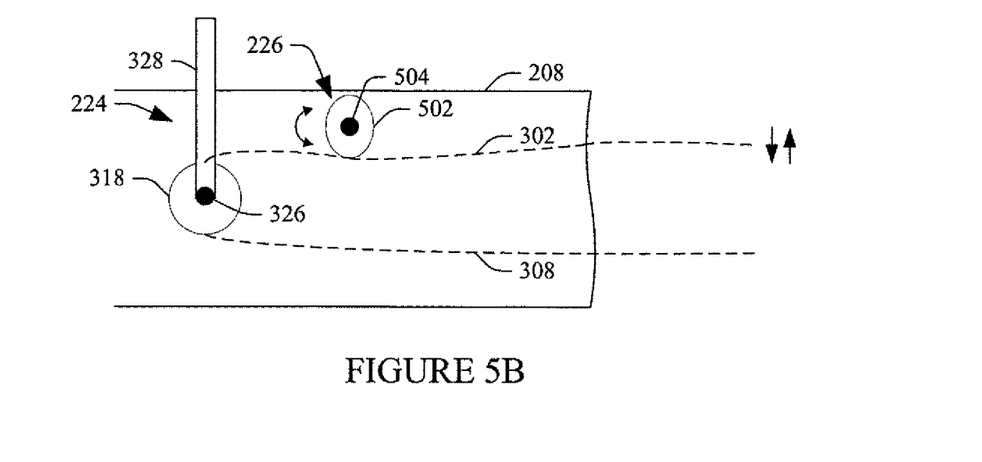

FIGS. 5A and 5B show another example of the motion actuator 226.

In this example, the motion actuator 226 includes a guide 502. The guide 502 is generally elliptical in shape, located at a fixed position, and configured to rotate about a pin 504. The guide 502 is located such that the guide 502 contacts the cable 302 at least when its long axis is perpendicular to the cable 302 (FIG. 5B). In this manner, rotating the guide 502 will vary the force on the cable 302 as a function of rotation angle as the guide 502 rotates, creating an oscillation.

The illustrated elliptical shape is not limiting. Generally, the member 502 can be any shape that will produce a varying force against the cable 302 while rotating the member 502, oscillating the cable 302. Examples of other shapes include triangular, rectangular, irregular, etc. More than one member 502 can be used can be used with the cable 302 and/or 308.

Figure 6A:
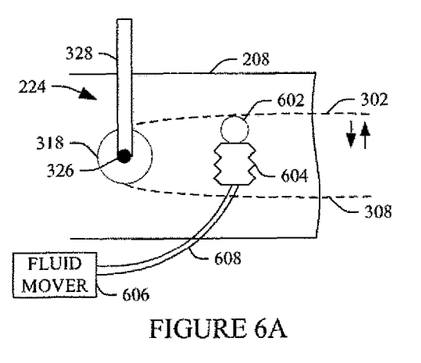
FIGS. 6A and 6B schematically illustrate another example of the motion actuator.
Figure 6B:
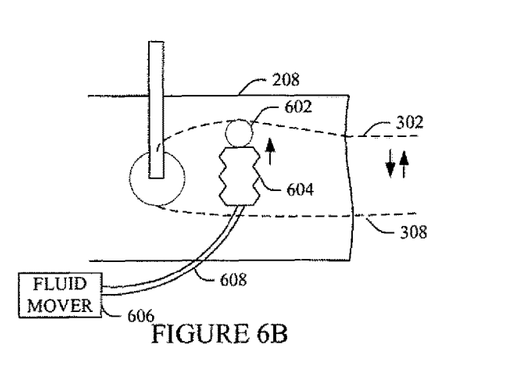

FIGS. 6A and 6B show another example of the motion actuator 226.

In this example, the motion actuator 226 includes a guide 602, which is in physical contact with the cable 302. An expandable/contractible chamber 604 is located adjacent to the guide 602. The chamber 604 is positioned such that when no fluid (e.g., air, gas, liquid, gel, etc.) is introduced into the chamber, either no or a minimum amount of force is exerted on the cable 302.

A fluid mover 606 moves a fluid (e.g., a liquid or gas) into and out of the chamber 604 via a pathway 608. The fluid mover 606 may include a manual or electric pump or the like which supplies and draws the fluid. The illustrated mover 606 is external. However, the mover 606 can alternatively be located in the probe 204. Similar to the mechanisms discussed above, the fluid mover 606 moves the cable 302 so as to apply a vibration to the cable 302 and have the probe head 214.

Optionally, the chamber 604 includes an egress port, which additionally or alternatively allows removal of the fluid from the chamber 604. FIG. 6A shows an empty chamber 604 and FIG. 6B shows a filled chamber 604.

Figure 7A:
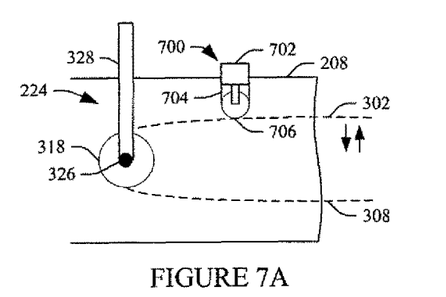
FIGS. 7A and 7B schematically illustrate another example of the motion actuator.
Figure 7B:
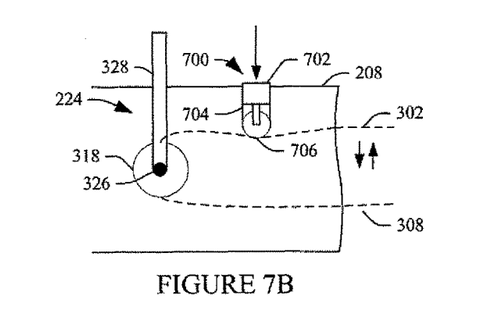

FIGS. 7A and 7B show another example of the motion actuator 226.

With this example, a pushbutton including slidable element 702 that is slideably coupled within a track 704 and affixed to a guide 706. In a non-pressed state (FIG. 7A), the pushbutton 700 exerts minimal (with respect to the force the guide 706 can exert on the cable 302) or no force on the cable. In a fully pressed state (FIG. 7B), the pushbutton 700 exerts a maximal (with respect to the force the guide 706 can exert on the cable 302) force on the cable 302.

During transition states between FIGS. 7A and 7B, the force applied by the guide 706 fluctuates or varies as a function of the relative position of the slidable element 702 in the track 704. Likewise, the slidable element 702 can be operated to move the cable 302 so as to apply a vibration to the cable 302 and have the probe head 214.

Figure 8A:
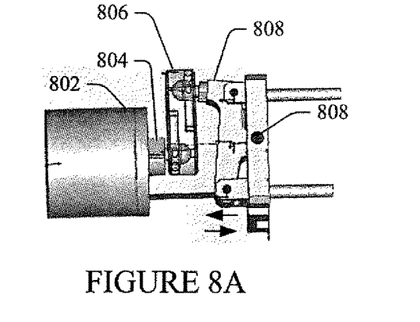
FIGS. 8A and 8B illustrate another example of the motion actuator.
Figure 8B:
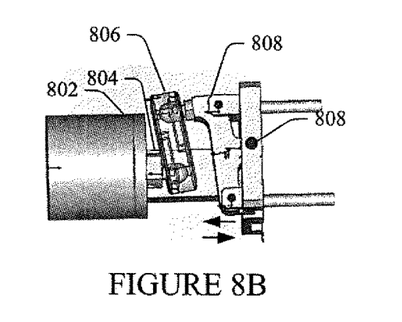

FIGS. 8A and 8B show another example of the motion actuator 226. In this example, a rotating motor 802 drives a rod 804 that is connected via a joint 806 such as a ball-joint or the like to a rocker arm 808 that converts the rotating movement into up/down movements via pivoting the rocker arm 808 about a pivot 810, which oscillates the at least one cable.

Figure 9:
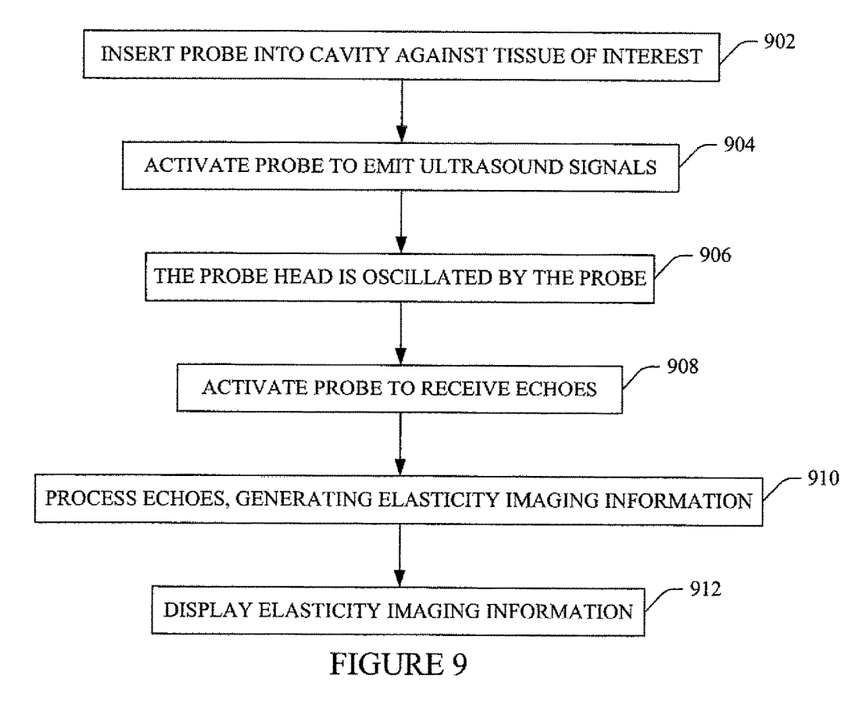
FIG. 9 illustrates an example method in accordance with the embodiments herein.

FIG. 9 illustrates a method for employing the probe 204 in connection with elasticity imaging.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 902, the probe 204 is inserted into a cavity of a subject or object.

At 904, the transducer array 216 is activated to emit ultrasound signals that traverse a field of view and an object or subject therein.

At 906, the probe head motion activator 226 is activated to vibrate the probe head 214. As discussed herein, the vibrating probe head causes a controlled fluctuating compression of the tissue.

At 908, the transducer array 216 is activated to emit receive echoes produced in response to interaction with the object or subject.

At 910, the console 206 processes the echoes, creating at least elasticity imaging information.

At 912, optionally, the console 206 visually displays the elasticity imaging information. In one instance, this may include visually displaying a B or other mode image with the elasticity imaging information superimpose or overlayed thereon.

The above may be implemented by way of computer readable instructions, encoded or embedded on computer readable storage medium such as physical memory or other non-transitory medium, which, when executed by a computer processor(s), cause the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An elongate ultrasound probe, comprising:
    a probe head with a transducer array;
    a handle;
    a flexor located between and affixed to the probe head and the handle;
    a flexor actuator configured to flex the flexor, wherein the flexor actuator includes at least one cable affixed to at least one side of the flexor, and the probe head motion actuator oscillates the at least one cable, which oscillates the cable, oscillating the probe head; and
    a probe head motion actuator configured to oscillate the flexor actuator and thereby oscillate the probe head, wherein the probe head motion actuator includes:
        first and second guides which support and are in physical contact with the at least one cable there between; and
        a control portion that oscillates the first and second guides, which oscillates the at least one cable.

2. The probe of claim 1, wherein probe head motion actuator oscillates the flexor actuator to oscillate the probe head at a frequency for ultrasound elasticity imaging.

3. The probe of claim 1, wherein oscillating the first and second guides fluctuates an amount of force applied to the at least one cable by the first and second guides.

4. The probe of claim 1, wherein the control portion is activated by at least one of the probe, an ultrasound console, or a remote device.

5. The probe of claim 1, wherein the control portion is electronically controlled.

6. A method, comprising:
    electronically vibrating a probe head, which includes a transducer array, of an ultrasound probe in connection with ultrasound elasticity imaging, wherein the ultrasound probe includes an articulating probe head in which two cables are utilized to flex the probe head, and at least one guide with two guides which support and are in physical contact with the at least one of the two cables there between, and wherein the electronically vibrating includes moving, in response to a signal, the at least one guide such that the at least one guide varies an amount of force applied to at least one of the two cable by oscillating the two guides, which oscillates the at least one of the two cables, thereby oscillating the at least one cable, which oscillates the probe head.

* * * * *